United States Patent
Han et al.

(10) Patent No.: US 7,754,479 B2
(45) Date of Patent: Jul. 13, 2010

(54) METHOD FOR CULTURING AVIAN SPERMATOGONIAL STEM CELLS AND AVIAN SPERMATOGONIAL STEM CELLS PREPARED THEREBY

(75) Inventors: Jae Yong Han, Seoul (KR); Yeong Ho Hong, Suwon-si (KR); Jeong Mook Lim, Seoul (KR); Young Mok Lee, Suwon-si (KR); Mak Soon Lee, Suwon-si (KR); Jin Gyung Jung, Seoul (KR)

(73) Assignees: Seoul National University Industry Foundation, Seoul (KR); Avicore Biotechnology Institute Inc., Gunpo (KR)

( * ) Notice: Subject to any disclaimer, the term of this patent is extended or adjusted under 35 U.S.C. 154(b) by 0 days.

(21) Appl. No.: 10/569,847

(22) PCT Filed: Aug. 6, 2004

(86) PCT No.: PCT/KR2004/001992

§ 371 (c)(1),
(2), (4) Date: Apr. 10, 2006

(87) PCT Pub. No.: WO2005/014802

PCT Pub. Date: Feb. 17, 2005

(65) Prior Publication Data

US 2007/0061910 A1    Mar. 15, 2007

(30) Foreign Application Priority Data

Aug. 8, 2003    (KR) .................. 10-2003-0055119

(51) Int. Cl.
*C12N 5/00*    (2006.01)
*C12N 5/07*    (2010.01)
*A01K 67/027*    (2006.01)

(52) U.S. Cl. .................. 435/325; 435/349; 800/19
(58) Field of Classification Search .............. 435/325, 435/349; 800/19
See application file for complete search history.

(56) References Cited

U.S. PATENT DOCUMENTS

| 6,156,569 A | 12/2000 | Ponce de Leon et al. |
| 6,316,692 B1 | 11/2001 | Readhead et al. |
| 2002/0162134 A1* | 10/2002 | Baguisi et al. ............ 800/19 |
| 2006/0265774 A1* | 11/2006 | Shinohara et al. ......... 800/24 |

FOREIGN PATENT DOCUMENTS

| WO | WO 03/024199 | 3/2003 |
| WO | WO 03/106651 | 12/2003 |

OTHER PUBLICATIONS

Izadyar et al. Biol. Reprod. 68:272-281, 2003.*
Shinohara et al. PNAS 97:8346-8351; 2000.*
Izadyar et al., "Proliferation and Differentiation of Bovine Type A Spermatogonia During Long-Term Culture," Biol. Reprod. 68:272-281, 2002.
Kanatsu-Shinohara et al., "Long-Term Proliferation in Culture and Germline Transmission of Mouse Male Germline Stem Cells," Biol. Reprod. 69:612-616, 2003.
Nagano et al., "Maintenance of Mouse Male Germ Line Stem Cells In Vitro," Biol. Reprod. 68:2207-2214, 2003.

* cited by examiner

*Primary Examiner*—Fereydoun G Sajjadi
(74) *Attorney, Agent, or Firm*—Clark & Elbing LLP

(57) ABSTRACT

The present invention relates to a method for long-term culturing of avian spermatogonial stem cells, which comprises the steps of: (a) preparing an avian testis; (b) isolating a population of testicular cells from said avian testis; and (c) culturing said avian spermatogonial stem cells in said population of testicular cells on a feeder cell layer in a medium containing a cell growth factor, a population of avian spermatogonial stem cells and a method for producing transgenic ayes.

15 Claims, 9 Drawing Sheets

METHOD FOR CULTURING AVIAN SPERMATOGONIAL STEM CELLS AND AVIAN SPERMATOGONIAL STEM CELLS PREPARED THEREBY

CROSS-REFERENCE TO RELATED APPLICATIONS

This application claims priority under 35 U.S.C. 371 from international application PCT/KR2004/001992, filed Aug. 6, 2004, which claims priority from Korean Patent Application 10-2003-0055119, filed Aug. 8, 2003.

BACKGROUND OF THE INVENTION

1. Field of the Invention

The present invention relates to a method for long-term culturing of avian spermatogonial stem cells, a population of avian spermatogonial stem cells and a method for producing transgenic aves.

2. Description of the Related Art

Spermatogenesis is a process involving division and differentiation of spermatogonial cells in testis of male animals and apoptosis of cells. Therefore, the spermatogenesis is very complex, systematic and effective process. The spermatogenesis in chicken is very similar to that of mammals, involving the complicated interaction between seminiferous tubule and interstitial cells.

Spermatogonial cells of avians originate from primordial germ cells (PGCs) that are derived from the epiblast and gradually move to the lower layer during the early stages of primitive streak formation. PGCs then translocate to the hypoblast and colonize at the germinal crescent. They circulate into the developing blood vascular system and migrate to the germinal ridge, finally differentiating into spermatogina in testis.

Spermatogonial cells have capacities of self-renewal and spermatogenesis (Morrison et al., 1997). In mice, a spermatogonial cell becomes spermatocyte through about ten times divisions. That is to say, a stem cell becomes 1024 spermatocytes and then 4096 spermatozoa following a series of meiosis. 75-95% of spermatozoa generated disappear by apoptosis.

Testes have a lower population of spermatogonial stem cells. For example, it has been suggested that $2 \times 10^4$ stem cells exist in a mouse testis having approximately $10^8$ cells (Meistrich & Beek, 1993; Tegelenbosch & de Rooij, 1993). A spermatogonial stem cell has become highlighted among spermatogonia because of its self-renewing and spermatogenesis potentials throughout adult life span.

Various attempts have been made to reproduce in vitro spermatogenesis using isolated germ cells; however, those have been finally unsuccessful. Rassoulzadegan et al., 1993 have reported that immature germ cells of rat are co-cultured with Sertoli cells to differentiate into haploid spermatid. However, there remain technical limitations in in vitro spermatogenesis. Hitherto, in vitro culture systems for spermatogonia have been reported to be practical only within several weeks (Ogawa, 2001; Dirmai et al., 1999; Nagano et al., 1998). It has been reported that spermatogonial cells were cultured for about 4 months and then introduced into a recipient to give rise to normal spermatogenesis (Nagano et al., 1998). The culturing of spermatogonial cells remains difficult because spermatogonial cells are isolated in a restrictive manner and its higher proportion dies during culture. In particular, morphological and biochemical markers to discriminate spermatogonial stem cells from spermatogonial cells differentiated have not yet been suggested, which is considered the greatest obstacle (Nagano et al., 1998; van Pelt et al., 2002).

Shinohara et al. (1999) have reported that antibodies against α6-integrin and β1-integrin show reactivity to spermatogonial stem cells from mice different from other tissue cells, demonstrating that they may serve as markers. DBA (*Dolichos biflorus* agglutinin) exhibits a specific reaction pattern for 30 weeks after birth to gonocyte and spermatogonia in bovine testis, ensuring the lectin may serve as markers (Ertl and Wrobel, 1992).

For mammals such as rat, spermatogonial cell line established by culturing has not been reported. Instead, there have a few reports in which spermatogonial cell lines of rat and mouse may be established using mTERT (mouse telomerase catalytic component) (Feng et al., 2002) or SV40 large T antigen (van Pelt et al., 2002).

Dobrinski et al. (2000) have cultured testicular cells from livestock such as cattle, pig and horse and then introduced cells into mouse testis. Izadyar et al. (2003) have studied the division and differentiation patterns of spermatogonial cells during long-term (about 150 days) culturing of bovine type A spermatogonial cells. The culture of spermatogonial cells from human has been performed mainly for treating diseases or disorders such as azospermia; however, where cells differentiated to spermatid were used for fertilization, it was observed that they did not develop to morula and lead to sex chromosome aberration (Sousa et al., 2002).

Meanwhile, avian spermatogonial cells become highlighted as a potential tool for producing transgenic avians; however, the culture and use of spermatogonial cells from avians such as chicken have not yet been researched. Such spermatogonial cells are expected to provide a tool to elucidate molecular mechanism of spermatogenesis and also to be useful in the production of transgenic animals and gene therapy of germ cells.

Throughout this application, various publications are referenced and citations are provided in parentheses. The disclosure of these publications in their entities are hereby incorporated by references into this application in order to more fully describe this invention and the state of the art to which this invention pertains.

DETAILED DESCRIPTION OF THIS INVENTION

Under such circumstances, the present inventors have made intensive researches to meet long-felt need in the art, and as a result, developed a novel method for culturing avian spermatogonial stem cells and identified avian spermatogonial stem cells prepared using the present method.

Accordingly, it is an object of this invention to provide a method for a long-term culture of avian spermatogonial stem cells.

It is another object of this invention to provide a population of avian spermatogonial stem cells.

It is still another object of this invention to provide a method for producing a transgenic ave by use of avian spermatogonial stem cells.

Other objects and advantages of the present invention will become apparent from the detailed description to follow and together with the appended claims and drawings.

In one aspect of this invention, there is provided a method for a long-term culture of avian spermatogonial stem cells, which comprises the steps of: (a) preparing an avian testis; (b) isolating a population of testicular cells from said avian testis; and (c) culturing said avian spermatogonial stem cells in said population of testicular cells on a feeder cell layer in a medium containing a cell growth factor.

The most striking feature of the present invention lies in the first breakthrough for culturing and identifying avian spermatogonial stem cells.

The present invention will be described in more detail with referring to each necessary step.

Step 1: Preparation of Avian Testis

Where the present invention is applied to chicken, testes to obtain testicular cells may be retrieved from male chickens aged of up to 70 weeks, preferably up to 20 weeks and more preferably 2-10 weeks. The testes of chickens may be obtained by isolating and dissecting the cervical vertebra.

Step 2: Isolation of Testicular Cell Population from Testis

A connective tissue and membrane around testes retrieved thus are removed and tunica albuginea is then removed. The testis was cut into pieces using an anatomic knife and disaggregated according to various protocols, resulting in the isolation of testicular cells.

The term used herein "testicular cell" refers to a cell population present in testis tissue including spermatogonial stem cell, any germ cell derived from spermatogonial stem cell, Sertoli cell, Leydig cell and muscle cell associated with connective tissue. There is no intended distinction between the terms "testicular cell" and "a population of testicular cells", and these terms will be used interchangeably.

The disaggregation of testis tissue may be performed in accordance with various conventional techniques. Preferably, the isolation of testicular cells from testes is carried out by treating avian testes tissues with collagenase, trypsin or their mixture. More preferably, it is carried out in accordance with a two-step enzymatic digestion, van Pelt method (1996) or collagenase-trypsin treatment described below. Most preferably, the isolation is carried out by collagenase-trypsin treatment described below.

① Two-Step Enzymatic Digestion

This process is carried out in accordance with the Ogawa et al. method (1997) or its modification. Testis tissues prepared are incubated with collagenase type I in HBSS (Hank's Balanced Salt's Solution, Invitrogen) and then treated with trypsin.

② van Pelt Method (1996)

For the disaggregation, testis tissues are incubated with collagenase type I, trypsin, hyaluronidase II and DNase I in DMEM.

③ Ad Collagenase-Trypsin Treatment

Collagenase and trypsin in HBSS are used to disaggregate testis tissues and pipetting is carried out for further disaggregation.

The disaggregation resultants obtained thus are filtered through a cell strainer (with a pore size of about 70 μm) to collect testicular cells.

Step 3: Culturing of Spermatogonial Stem Cells in Population of Testicular Cells The testicular cells prepared are cultured in a medium containing a cell growth factor.

For culturing of avian spermatogonial stem cells, a feeder cell layer is essentially required and avian spermatogonial stem cells are proliferated with attached onto a feeder cell layer to form colonies. According to a preferred embodiment, the feeder cell is fibroblast, gonadal stroma cell, testicular stroma cell or mouse STO cell line (SIM mouse embryo-derived, Thioguanine- and Quabain-resistant fibroblast cell line), more preferably, gonadal stroma cell or testicular stroma cell and most preferably, gonadal stroma cell. Where the present invention is applied to chickens, it is preferred that fibroblast, gonadal stroma cell and testicular stroma cell are chicken-derived.

The feeder cells are placed at the bottom of dishes or plates containing a medium and avian spermatogonial stem cells transferred to medium are proliferated with attached onto the feeder cell layer.

A medium for culturing of avian spermatogonial stem cells comprises a growth factor as an essential ingredient. Preferably, the medium comprises fibroblast growth factor, insulin-like growth factor-1, stem cell factor, glia-derived neurotrophic factor or their combination. More preferably, the medium comprises fibroblast growth factor, insulin-like growth factor-1, stem cell factor or their combination. Most preferably, the medium comprises a mixture of fibroblast growth factor and insulin-like growth factor-1. According to a preferred embodiment, the medium used in this invention further comprises a differentiation inhibitory factor, most preferably, leukemia inhibitory factor. Therefore, the most preferable combination of a growth factor and differentiation inhibitory factor contained in the medium is a mixture of fibroblast growth factor, insulin-like growth factor-1 and leukemia inhibitory factor.

In addition, the medium used in this invention further comprises an avian serum (e.g., chicken serum), mammalian serum (e.g., calf fetal serum) or their mixture. It is preferred that antioxidants (e.g., β-mercaptoethanol), antibiotics-antimycotics, non-essential amino acids (e.g., arginine, asparagine, aspartic acid, glutamic acid, glycine, proline and serine), buffer (e.g., Hepes buffer) or their combination are used in the medium.

In the culturing step of this invention, the culturing temperature is most preferably about 37° C. The most preferable culture temperature is recognized unique in the senses that the body temperature of chicken is 41° C.

In the meantime, a primary culture of avian spermatogonial stem cells may be performed prior to the culturing step (c).

Step 4: Identification of Avian Spermatogonial Stem Cells

The cells cultured in the previous steps are characterized to identify spermatogonial stem cells.

The identification is carried out by (i) PAS (Periodic Acid Shiff's) staining, (ii) STA (*Solanum tubersum* agglutinin) staining, (iii) a staining with α6-integrin antibody, (iv) a staining with β1-integrin antibody, (v) a staining with anti-SSEA-1 antibody, (vi) a staining with anti-SSEA-3 antibody, (vii) a staining with anti-SSEA-4 antibody, (viii) DBA (*Doliclos bifflrus* agglutinin) staining or (ix) their combination. For enhancing a reliability of the identification, it is preferred that various combinations of the staining methods described previously are carried out.

(i) PAS Staining

Spermatogonial stem cells cultured are fixed in a fixation solution (containing phosphate buffer, glutaraldehyde, formaldehyde and $MgCl_2$) and incubated with a periodic acid solution, followed by staining with Shiff's reagent. The cytoplasm stained purplish red represents a positive reaction with PAS staining, making it possible to identify avian spermatogonial stem cells.

(ii) STA or DBA Staining

Spermatogonial stem cells are fixed in a fixation solution and incubated with STA (*Solanum tubersum* agglutinin) or DBA (*Doliclos bifflrus* agglutinin) conjugated with a fluorescent substance (e.g., FITC (fluorescein isothiocyanate)), e.g., FITC-STA or FITC-DBA. The observation under a fluorescence microscope is performed. A fluorescence observed on the surface of cells represents a positive reaction with STA or DBA staining, enabling avian spermatogonial stem cells to be identified.

(iii) α6-Intergrin Antibody Staining

Spermatogonial stem cells are treated with a primary antibody, α6-integrin antibody (Sigma) and then a secondary antibody (capable of binding to Fc domain of antibodies, e.g., goat anti-mouse IgG) conjugated with a label, e.g., a fluorescent substance (e.g., TRITC (tetramethyl rhodamine isothiocyanate)). The observation under a fluorescence microscope is performed. A fluorescence observed on the surface of cells represents a positive reaction with anti-α6-intergrin antibody staining, enabling avian spermatogonial stem cells to be identified.

(iv) β1-Intergrin Antibody Staining

The staining with anti-β1-intergrin antibody is carried out in the same manner as that with α6-integrin antibody staining, except that anti-β1-intergrin antibody is used as a primary antibody.

(v) Anti-SSEA-1, SSEA-3 and SSEA-4 Antibody Staining

Spermatogonial stem cells are incubated with a primary antibody, anti-SSEA-1, SSEA-3 or SSEA-4 antibody and then a secondary antibody conjugated with a catalyst for color development reaction (e.g., alkaline phosphatase). After the addition of a substrate for the catalyst, the calorimetric reaction is measured. The color development represents a positive reaction with anti-SSEA-1, SSEA-3 or SSEA-3 antibody staining, enabling avian spermatogonial stem cells to be identified.

The present invention is useful in culturing of spermatogonial stem cells derived from a wide variety of avian species, preferably, a chicken, a quail, a turkey, a duck, a goose, a pheasant and a pigeon, most preferably, a chicken.

According to the present invention, avian spermatogonial stem cells can be cultured for at least 2 months, preferably at least 3 months, more preferably at least 4 months and most preferably at least 5 months.

The present method provides avian spermatogonial stem cells in a more reliable manner. Accordingly, in another aspect of this invention, there is provided a population of avian spermatogonial stem cells comprising avian cells expressing characteristics of a spermatogonial stem cell.

The term used herein "a population of avian spermatogonial stem cells" means a cell population consisting essentially of avian spermatogonial stem cells. That is, the population of avian spermatogonial stem cells of this invention includes a cell population containing only avian spermatogonial stem cells as well as a cell population containing avian spermatogonial stem cells and a minor number of other types of cells, e.g., spermatogonial cells.

The characteristics of a spermatogonial stem cell include a positive reaction to (i) PAS (Periodic Acid Shiff's) staining, (ii) STA (*Solanum tubersum* agglutinin) staining, (iii) a staining with α6-integrin antibody, (iv) a staining with β1-integrin antibody, (v) a staining with anti-SSEA-1 antibody, (vi) a staining with anti-SSEA-3 antibody, (vii) a staining with anti-SSEA-4 antibody, (viii) DBA (*Doliclos bifflrus* agglutinin) staining or (ix) their combination.

In still another aspect of this invention, there is provided a method for producing a transgenic ave, which comprises the steps of: (a) transferring a foreign gene to the population of avian spermatogonial stem cells of this invention; (b) transplanting said population of avian spermatogonial stem cells into a testis of a recipient; and (c) producing a progeny from said recipient to produce the transgenic ave.

In the present method, the step of transferring a foreign gene to the population of avian spermatogonial stem cells is performed in accordance with various conventional approaches for gene transfer. For example, electroporation, liposome-mediated transformation (Wong et al., 1980) and retrovirus-mediated transformation (Chen et al., 1990; Kopchick et al., 1991; Lee & Shuman, 1990) are useful in gene transfer. It is most preferred that the electroporation method is performed according to the procedures suggested by the present inventors (see, Korean Patent No. 305715).

According to a preferred embodiment, the foreign gene carries an antibiotic-resistance gene as a selection marker. It is preferred that the present method further comprises the step of selecting spermatogonial stem cells exhibiting the antibiotic resistance property after step of (a), and the step of (b) is then conducted using the antibiotic resistant spermatogonial stem cells. The selective marker useful in this invention may include any gene conferring antibiotic resistance property to eucaryotic cells, for example, neomycin-, puromycin- and zeomycin-resistance genes.

It is preferred that the step of transplanting avian spermatogonial stem cells into the testis of the recipient is carried out by microinjecting spermatogonial stem cells into the seminiferous tubules.

The recipient is mated with other individual to generate progenies, finally producing a transgenic ave harboring the foreign gene.

EXAMPLES

Figure 1:
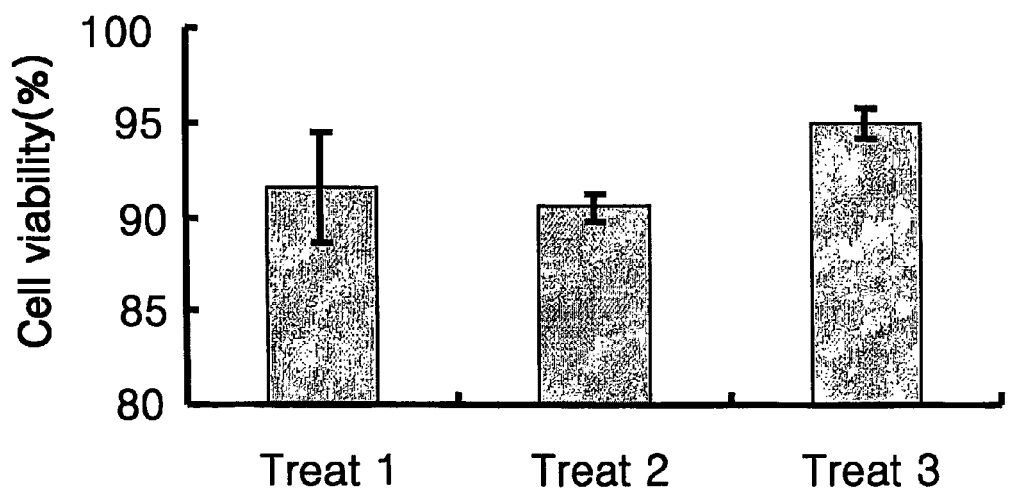
FIG. 1 is a graph representing cell viability depending on methods for disaggregating chicken testis tissue. Treat 1: a two-step enzymatic digestion, Treat 2: van Pelt method (1996), and Treat 3: collagenase-trypsin treatment.

The following specific examples are intended to be illustrative of the invention and should not be construed as limiting the scope of the invention as defined by appended claims.

Materials and Methods

1) Donor Chicken and Isolation of Testis

Chickens for culturing spermatogonial stem cells were White Leghorn males maintained at Avicore Biotechnology Institute Inc. The testes of chickens were obtained by dissecting vertebrae cervicales of donor chicken. The weights of body and testis depending on age were measured.

2) Comparison of Disaggregation Method of Testis Tissue

The connective tissue and membrane around the testis isolated were removed and tunica albuginea was then removed using microforceps. The testis was cut into pieces using anatomic knife under a stereomicroscope and disaggregated according to various protocols.

① Disaggregation by Two-Step Enzymatic Digestion

This protocol was carried out with a little modification of the Ogawa et al. method (1997). Testis tissues prepared were subject to the treatment of collagenase (1 mg/ml, Sigma) in HBSS (Hank's Balanced Salt's Solution, Invitrogen) and incubated for 15 min at 37° C. in shaking incubator. Thereafter, testis tissues were washed with HBSS and trypsinized (0.25% trypsin-1 mM EDTA; Invitrogen). The released testicular cells were collected by filtering through 70 μm cell strainer (Falcon 2350) and their viability and number were measured using trypan blue.

② Disaggregation Using van Pelt Method (1996)

Testis tissues prepared above were treated for 15 min with collagenase (1 mg/ml, Sigma), trypsin (1 mg/ml, Sigma), hyaluronidase II (1 mg/ml, Sigma) and DNase I (5 μg/ml, BMS) dissolved in DMEM (Invitrogen) for 150 cycles/min. The tissues were washed three times with DMEM and subject to the second digestion with collagenase (1 mg/ml, Sigma), hyaluronidase II (1 mg/ml, Sigma) and DNase I (5 μg/ml, BMS) dissolved in DMEM for 30 min, completely disaggregating testis tissues. The released testicular cells were collected by filtering through 70 μm cell strainer and their viability and number were measured.

③ Collagenase-Trypsin Treatment

Cells were disaggregated in lysis media containing collagenase (1 mg/ml, Sigma) and 0.25% trypsin in HBSS (Invitrogen). Testis tissues were disaggregated for 30 min at 37° C. in a shaking incubator at 150 rpm with pipetting at an interval 5 min. 10% FCS (fetal calf serum) was added to terminate enzyme activities and the resultant was filtered through a cell strainer (70 μm, Falcon 2350). The testicular cells thus obtained were analyzed in terms of their viability and number.

3) Distribution of Spermatogonial Stem Cells in Testis Tissue

For observing morphology of testis tissues and distribution pattern of spermatogonial stem cells depending on the week age of chicken, the characterization of testis tissues was done by performing tissue analysis and the number of spermatogonial stem cells was measured using STA (*Solanum tuberosum* agglutinin).

There is little known about the number of spermatogonial stem cells in avian testis tissue. To measure the number of spermatogonial stem cells, the testis from 3-week-old White Leghorn was disaggregated using collagenase-trypsin and testicular cells thus obtained were fixed for 5 min using 0.5% paraformaldehyde. The cells were incubated for 2 hr with FITC-conjugated STA (*Solanum tuberosum* agglutinin, Sigma), lectins specific to spermatogonial stem cells. The distribution of spermatogonial cells in total testicular cells was analyzed by measuring the number of cells with fluorescence ascribed to STA.

4) Comparison of Feeder Cells

Because the testicular cells primarily cultured for 7-10 days have to be transferred to a suitable feeder layer for further culture, the comparison of feeder cells was performed to select the most suitable feeder layer for culturing chicken testicular cells. Testis tissues were obtained from 2-4-week old male chicken and disaggregated according to the collagenase-trypsin treatment described above. The testicular cells thus obtained were analyzed in terms of their viability and number and seeded into culture dishes (100 mm) at $2 \times 10^6$ cells per dish, followed by culturing for 8-10 days. The composition of media used was the same as that of the most preferred media for spermatogonial stem cell culture described below, except for no addition of feeder cells. $6-8 \times 10^4$ cells/well of chicken embryonic fibroblast (CEF), gonadal stroma cell (GSC) or testicular stroma cell (TSC) as feeder cells were cultured in 6-well plates (TPP, EU). Mouse STO cell line (ATCC CRL-1503) treated with mitomycin-C (10 μg/ml) to arrest cell division was used. $1 \times 10^5$ cells/well of the primary cultured spermatogonial stem cells were further cultured on the feeder layer for 8-10 days at 37° C. in 5% $CO_2$ incubator and their number were then measured for statistics.

5) Establishment of Medium Composition for Culturing

To establish culturing conditions in view of medium composition for chicken spermatogonial stem cells, the cultures of spermatogonial stem cells were evaluated depending on a medium composition.

(i) DMEM-B (Basic Medium)

For the preparation of a basic medium, 10% (v/v) fetal bovine serum (FBS, Hyclone, Logan Utah) for ES cells and 1× antibiotics-antimycobacteria agent (Invitrogen) were added to DMEM (Invitrogen).

(ii) DMEM-C (Supplement)

2% chicken serum (Invitrogen), 10 mM non-essential amino acids (Invitrogen), 10 mM Hepes buffer (Invitrogen)

and 0.55 mM β-mercaptoethanol (Invitrogen) were added to the basic medium indicated above.

(iii) $1\times10^4$ cells/well of spermatogonial stem cells at passage 1 in 24-well plates were cultured on GSC feeder layer ($8\times10^3$ cells/well) for 9 days at 37° C. in 5% $CO_2$ incubator up to 5 passages and the colonies formed were counted.

6) Establishment of Optimal Culture Conditions in Terms of Supplements

To establish the optimal culture conditions, the influence of each growth factor on the cultivation of chicken spermatogonial stem cells was examined.

(i) The culturing was performed at 37° C. in 5% $CO_2$ incubator using DMEM-C (control) described previously supplemented with 10 ng/ml human leukemia inhibitory factor (Sigma), 10 ng/ml human basic fibroblast growth factor (Sigma), 100 ng/ml human insulin-like growth factor-1 (Sigma), 20 ng/ml human stem cell factor (Sigma) or 1100 ng/ml human glia-derived neurotrophic factor (R&D system, USA).

(ii) Spermatogonial stem cells ($1\times10^4$ cells/well) at passage 1 in 24-well plates were cultured for 9 days on GSC feeder layer ($8\times10^3$ cells/well) up to 3 passages and the colonies formed were counted.

7) Influence of Culture Temperature on Culture of Spermatogonial Stem Cells

To reveal the optimal temperature for culturing chicken spermatogonial stem cells, the culturing pattern was examined at 41° C. (body temperature of aves) or 37° C. (general culture temperature). SSC medium, i.e., DMEM-C supplemented with 2 ng/ml human leukemia inhibitory factor (Sigma), 5 ng/ml human basic fibroblast growth factor (Sigma) and 10 ng/ml human insulin-like growth factor-1 (Sigma) was used. Testicular cells obtained from 3-week-old White Leghorn were primarily cultured for 10 days and spermatogonial stem cells were then harvested. The number of spermatogonial stem cells was measured.

8) Growth Curve of Chicken Spermatogonial Stem Cells

Chicken spermatogonial stem cells were cultured using the optimal culture temperature, medium and feeder cell layer established for in vitro culturing of chicken spermatogonial stem cells and their number was measured in the course of culturing day.

$2.0\times10^6$ cells/dish (100 mm) of cells obtained by the disaggregation of testis tissue were subcultured on GSC feeder cell layer at an interval of about 10 days in the medium for spermatogonial stem cells and the number of spermatogonial stem cells was recorded.

9) Characterization of Spermatogonial Stem Cells by Immunocytochemical Methods

To elucidate the characteristics of chicken spermatogonial stem cells cultured, PAS (Periodic Acid Schiff's) staining kit (Sigma), STA (Sigma), chicken anti-integrin β1 antibody (Sigma) and chicken anti-integrin α6 antibody (Chemicon International. Inc, USA) were used (i) PAS (Periodic Acid Shiff's) Staining The spermatogonial stem cells cultured were fixed for 10 min in a fixation solution (50 mM phosphate buffer, 2% glutaraldehyde, 2% formaldehyde and 2 mM $MgCl_2$) and rinsed three times with PBS. The cells then incubated for 5 min in a periodic acid solution and rinsed three times with PBS. Finally, the cells were immersed for 10-15 min in Shiff's Solution (Sigma) and washed with PBS, followed by the observation under a microscope.

(ii) STA (*Sojanum tuberosum* Agglutinin) Staining

The spermatogonial stem cells were fixed with the fixation solution and incubated with FITC-STA (Sigma, 50 μg/ml) for 1 hr at room temperature. After washing three times with PBS, the cells were observed under a fluorescence microscope (Nikon TE2000-U, Japan).

(iii) α6-Intergrin and β 1-Integrin Staining

The spermatogonial stem cells fixed were rinsed with PBS and incubated for 1 hr at room temperature with 2% normal goat serum for blocking. Then, the cells were treated for 1 hr at room temperature with a primary antibody, 20 μg/ml α6-integrin antibody (Chemicon Int.) and β1-integrin antibody (Sigma). The cells were incubated for 1 hr at room temperature with a secondary antibody, TRITC (tetramethyl rhodamine isothiocyanate)-conjugated goat anti-mouse IgG (Jackson Lab) and observed under a fluorescence microscope.

(iv) Anti-SSEA-1, SSEA-3 and SSEA-4 Antibody Staining

The spermatogonial stem cells treated with the fixation solution were washed with PBS and treated with Levamisole. To minimize nonspecific binding of a secondary antibody, the blocking was performed for 30 min at room temperature using 5% goat serum. Then, the cells were incubated for 1 hr at room temperature with a primary antibody, 1:100 diluted anti-SSEA-1 antibody (MC-480) or anti-SSEA-4 antibody, or 1:200 diluted anti-SSEA-3 antibody (MC-631) (MC-813-70; Developmental Studies Hybridoma Bank, Iowa, Iowa). A secondary antibody goat anti-mouse IgM-AP (AK-5010, Vector Laboratories, Inc., Burlingama, Calif.) was then treated. The resultant was reacted with ABC solution for 30 min and then with BCIP/NBT (Sigma) substrate for 30 min and the reaction was stopped by adding 10 mM EDTA (pH 8.0).

(v) Double Immunostaining

The spermatogonial stem cells were treated with anti-SSEA-1, SSEA-3 or SSEA-4 antibody and then with a secondary antibody, rhodamine (TRITC)-conjugated goat anti-mouse IgG (115-025-003, Jackson ImmunoResearch Laboratories. Inc, Bar Harbor, Me.). Thereafter, cells were washed three times with PBS and treated for 1 hr with FITC-STA, followed by the observation under a fluorescence microscope.

Results

1) Comparison of Methods for Isolation of Testicular Cell

To obtain testicular cells, chicken testis tissues were disaggregated in accordance with enzymatic methods including two-step enzymatic method (Ogawa et al., 1997), van Pelt method (1996) and the method using a mixture of collagenase and trypsin. The testicular cells isolated included germ cells and somatic cells and their viability was analyzed using trypan blue (see Table 1 and FIG. 1). Compared with the results of three types of the disaggregation methods, it could be appreciated that the method using a mixture of collagenase (1 mg/ml) and trypsin (0.25%) exhibited the highest cell viability. Moreover, the method could be carried out in more convenient and shorter time manner than other two methods including two-step enzymatic method and van Pelt method. Therefore, it could be recognized that the method using a mixture of collagenase and trypsin is the most effective process for disaggregating chicken testis tissues.

TABLE 1

Viability and number of testicular cells depending on methods for disaggregating chicken testis tissue

| No. of experiment | Viability (%) | | |
|---|---|---|---|
| times | Method 1 | Method 2 | Method 3 |
| 1 | 91.4 | 89.9 | 94.1 |
| 2 | 88.5 | 91.1 | 95.8 |
| 3 | 90.7 | 91.0 | 94.5 |
| 4 | 95.5 | 89.8 | 95.5 |
| Mean ± SD | 91.5 ± 2.92 | 90.5 ± 0.70 | 95.0 ± 0.81 |

2) Distribution of Spermatogonial Stem Cells in Testis Tissue

Up to now, little has been known about the number of spermatogonial stem cell in testis of aves such as chicken and it has been merely presumed that the spermatogonial stem cells are present in a very small number. In mice, it has been suggested that approximately $2 \times 10^4$ stem cells are present in testis containing about $10^8$ cells (Meistrich & Beek, 1993; Tegelenbosch & de Rooij, 1993). The cells positive toward STA-FITC staining were counted to measure the number of spermatogonial stem cells in chicken testis tissue (see Table 2).

Because aves such as chicken also have no reliable morphological and molecular markers like mammals, various lectins (STA, WGA, DBA, ConA) were tested to reveal their specificity toward chicken spermatogonial stem cell. As a result, it was elucidated that FITC-STA (*Sojanum tuberosum* agglutinin) was reacted with chicken spermatogonial stem cells in a specific manner. The results of STA staining led us to reason that about 0.8% of chicken testicular cells is a spermatogonial stem cell. Therefore, it would be understood that approximately $8 \times 10^4$ stem cells of about $10^7$ testicular cells may exist in 2-3 week-old White Leghorn, although some variations may be anticipated depending on breed and week age of chicken. The percentage of the number of spermatogonial stem cells in chicken testicular cells is about 40-fold larger than that of mouse (0.02%). Such high population of chicken spermatogonial stem cells is considered to be significantly useful in in vitro culture, establishment of cell line and genetic manipulation of chicken spermatogonial stem cells.

TABLE 2

Number of spermatogonial stem cells in testicular cells specifically reactive to FITC-STA

| No. of cells stained with FITC-STA | Total cell no. | Percentage (%) |
|---|---|---|
| 8 | 918 | 0.88 |
| 6 | 823 | 0.73 |
| 5 | 637 | 0.78 |
| — | Mean ± SD | 0.80 ± 0.076 |

Figure 2:
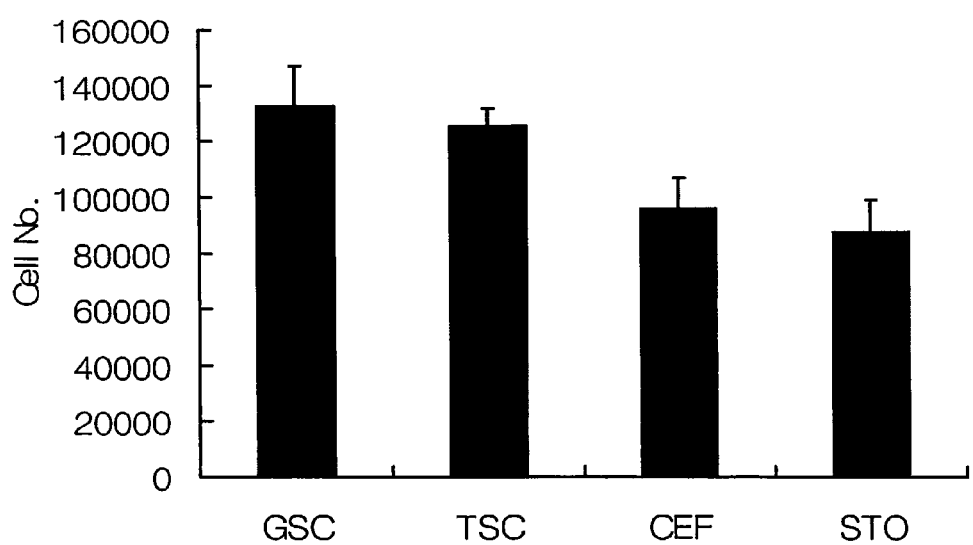
FIG. 2 is a graph representing culture patterns of chicken spermatogonial stem cells depending on a type of feeder cells. Spermatogonial stem cells primarily cultured were cocultured with each type of feeder cells for 8 days and their number was counted.

3) Determination of Optimal Feeder Cells for Culturing Spermatogonial Stem Cells There is no report about the culture of spermatogonial stem cells of aves such as chicken. We attempted to culture chicken spermatogonial stem cells in other approach than mouse spermatogonial stem cells. Since spermatogonial stem cells are derived from PGC, the medium was prepared with some modifications of EG medium (Park et al., 2000). The culture of PGC, embryonic germ cells and testicular cells is dependent upon feeder cells and various feeder cells including chicken embryonic fibroblast (CEF), chicken gonadal stroma cell (GSC), chicken testicular stroma cell (TSC) and mouse STO cell line were therefore compared to determine the most suitable feeder cells (see FIG. 2).

Following the primary culture and passage 1 culture, the spermatogonial stem cells were cocultured with feeder cells and were counted. The spermatogonical stem cells cocultured with GSC showed the highest population although there was no significant difference compared to TSC. The coculture with CEF and STO exhibited the lowest population of spermatogonical stem cells. Therefore, it was revealed that GSC is the most suitable feeder cell in the culture of spermatogonical stem cells. In addition, it could be recognized that although the coculture with Sertoli cells serving as nurse cells secures the provision of growth factors necessary to proliferate and develop spermatogonical stem cells (Sousa et al., 2002; van der Wee et al., 2001; Rassoulzadegan et al., 1993), the coculture with Sertoli cell-derived cell lines such as TM4 and SF7 results in the decrease of the viability of spermatogonial stem cells compared to other cell lines because Sertoli cell-derived cell lines induce the differentiation of spermatogonial stem cells (Nagano et al., 2003).

TSC showed the most preferred culture behavior for testicular cells isolated from 3-week-old chicken and CEF was likely to be curled due to its higher growth rate and detached together with colony isolation. Even though STO has been known the best feeder cell for stem cells of mice and mammals, the culture of chicken spermatogonial stem cells with mitomycin-treated STO resulted in a worse colony formation than other feeder cells and led to continuous detachment of a small number of cells.

4) Establishment of Culture Conditions in View of Media Composition

Figure 3:
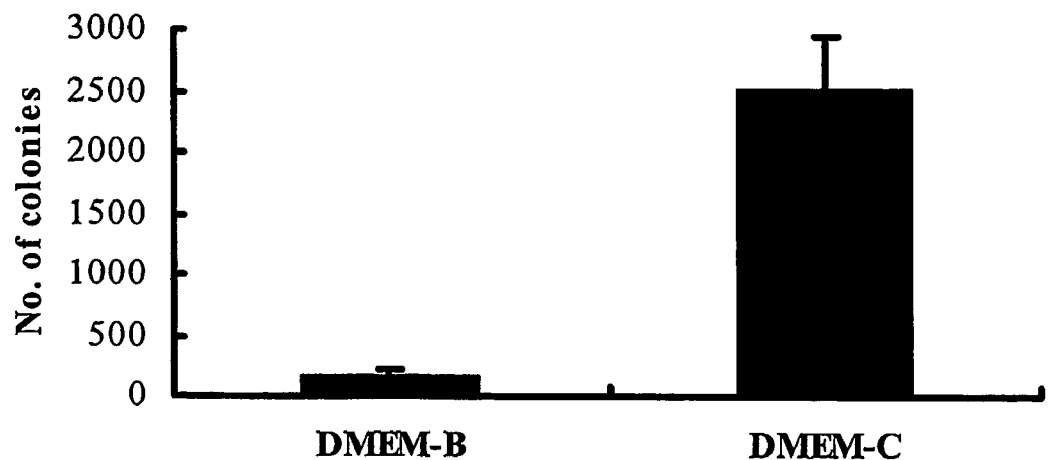
FIG. 3 is a graph representing the number of colonies originated from chicken spermatogonial stem cells depending on the composition of media.

To establish culture conditions in view of media composition for chicken spermatogonial stem cells, spermatogonial stem cells were culture for 9 days in the basic medium (DMEM-B) and supplemented medium (DMEM-C) and the number of colonies formed was counted. DMEM-C formed about 14-fold colony number more than that of DMEM-B (see Table 3 and FIG. 3).

Such higher population is ascribed to the supplements in DMEM-C medium including chicken serum, non-essential amino acids (metabolic substrate), Hepes buffer and antioxidant and β-mercaptoethanol. In contrast, Nagano et al. (2003) reported that the culture of mouse spermatogonial stem cells using media containing basic medium, metabolic substrates and buffer is not different from that using basic medium; however, two media exhibited considerably different culture pattern described above.

Figure 4:
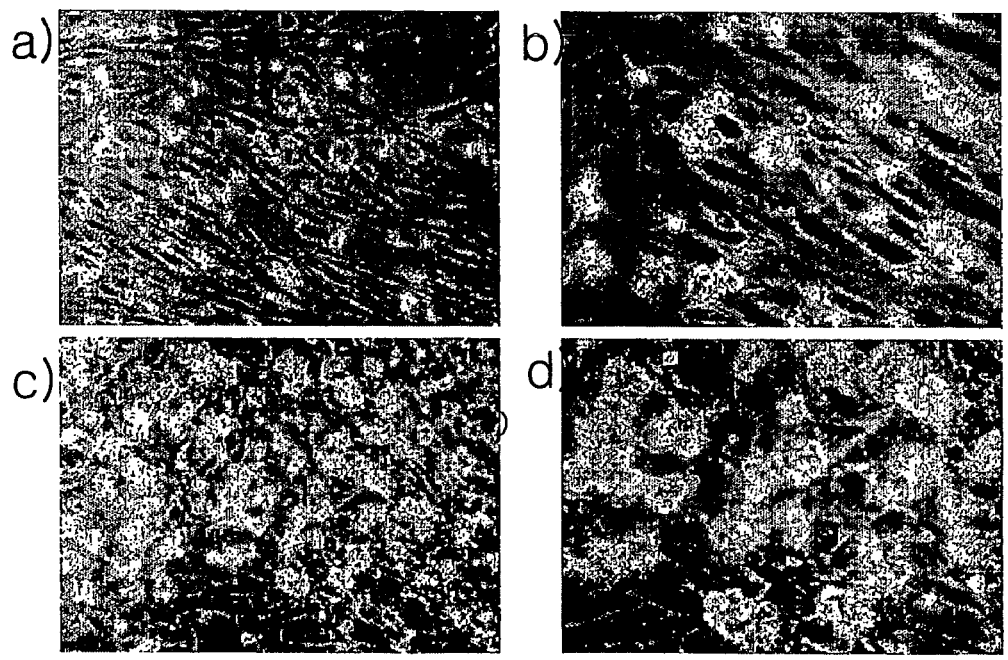
FIG. 4 is photographs showing the morphology of cultured chicken spermatogonial stem cells depending on the composition of media. a-b: DMEM-B medium, c-d: DMEM-C medium (a,c: 100x, b,d: 200x).

With regard to the appearance of cells, most of cells cultured in DMEM-B remained a single cell and their size became smaller (see FIGS. 4(*a*) and (*b*)). By contrast, cells cultured in DMEM-C formed colonies prosperously and their morphology and size remained the same as those of spermatogonial stem cells at passage 0 (see FIGS. 4(*c*) and (*d*)).

TABLE 3

Comparison of colony number depending on medium composition

| No. of experiment times | DMEM-B | DMEM-C |
|---|---|---|
| 1 | 212 | 2652 |
| 2 | 192 | 2636 |
| 3 | 172 | 2816 |

TABLE 3-continued

Comparison of colony number depending on medium composition

| No. of experiment times | DMEM-B | DMEM-C |
|---|---|---|
| 4 | 144 | 1836 |
| 5 | 140 | 2332 |
| Mean ± SD | 172 ± 30.8 | 2514 ± 411 |

5) Establishment of Optimal Culture Conditions in View of Supplements

To establish the optimal culture conditions, the influence of each growth factor on the culture of chicken spermatogonial stem cells was examined. Stem cell factor (SCF), leukemia inhibitory factor (LIF) and basic fibroblast growth factor (bFGF) have been already reported to promote maintenance and proliferation of PGC (Matsui et al., 1992; Resnick et al., 1992), and GDNF has been elucidated to play a critical role in the control of in vivo differentiation of spermatogonial stem cells (Meng et al., 2000; Nagano et al., 2003).

To evaluate the influence of each growth factor, the culture was performed for about 9 days in 24-well plates and the number of colonies formed was counted.

(i) DMEM-C (control)
(ii) DMEM-C+LIF (10 ng/ml)
(iii) DMEM-C+bFGF (10 ng/ml)
(iv) DMEM-C+SCF (20 ng/ml)
(v) DMEM-C+IGF-1 (100 ng/ml)
(vi) DMEM-C+GDNF (100 ng/ml)

Figure 5:
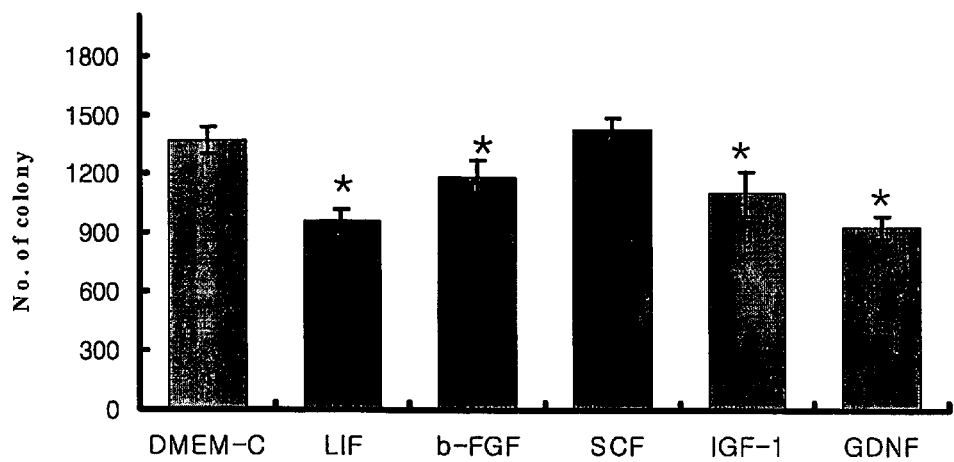
FIG. 5 is a graph representing the number of colonies originated from chicken spermatogonial stem cells depending on growth factors (*: P<0.05).

As the results of counting colonies of spermatogonial stem cell in each well, the control medium led to the formation of more colonies than those supplemented with LIF, bFGF, IGF-1 or GDNF and the medium supplemented with SCF formed the largest number of colonies (see Table 4 and FIG. 5). Such results urged us to reason that SCF does not affect rather than elicits the division of chicken spermatogonial stem cells (Ohta et al., 2000). Compared the results from the control medium, it could be recognized that LIF, bFGF and IGF-1 do not affect the division and growth of chicken spermatogonial stem cells. These results are similar to those observed in the culture of mouse spermatogonial stem cells (Nagano et al., 2003). GDNF has been reported to result in accumulation of undifferentiated spermatogonial stem cells through the inhibition of differentiation (Meng et al., 2000) and affect more positively the culture of mouse spermatogonial stem cells than other growth factor. However, it was revealed that GDNF exhibits the lowest proliferation effect in culture of chicken spermatogonial stem cells (see Table 4 and FIG. 5).

The control medium showed relatively favorable culture pattern in view of colony formation and number; however, the medium supplemented with LIF, IGF-1 or GDNF resulted in worse colony formation and less colony number than the control medium, although the significant difference was not found among culture patterns of growth factors.

TABLE 4

Comparison of colony number of spermatogonial stem cells depending on growth factors

| No. of experiment times | No. of colony | | | | | |
|---|---|---|---|---|---|---|
| | DMEM-C | LIF | bFGF | SCF | IGF-1 | GDNF |
| 1 | 1368 | 892 | 1096 | 1392 | 1148 | 880 |
| 2 | 1304 | 976 | 1212 | 1492 | 980 | 924 |
| 3 | 1440 | 1008 | 1252 | 1392 | 1188 | 1000 |
| Mean ± SD | 1370 ± 68 | 958 ± 59 | 1186 ± 81 | 1425 ± 57 | 1105 ± 110 | 934 ± 60 |

Figure 6:
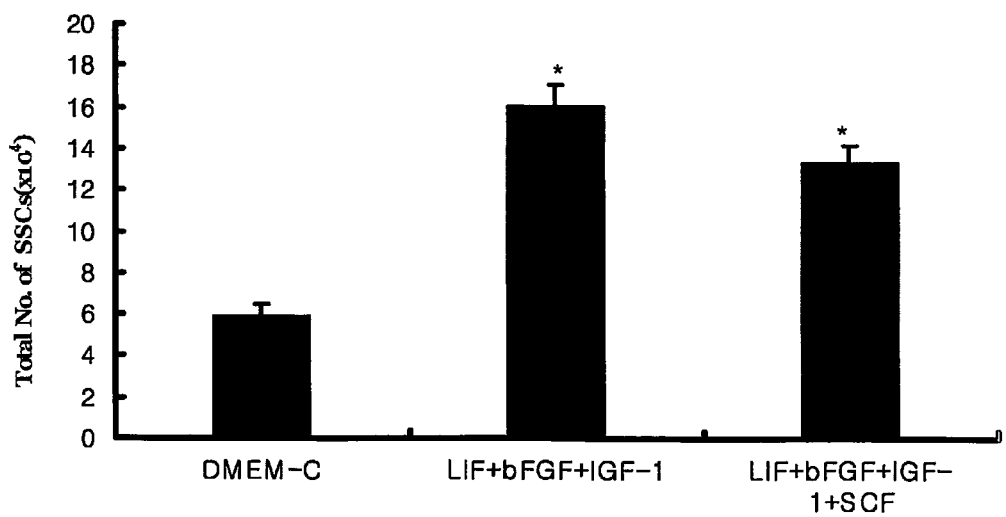
FIG. 6 is a graph showing the number of chicken spermatogonial stem cells depending on combinations of growth factors (*: P<0.001).

Each growth factor exerts synergic effect by its interaction with other growth factors. LIF has been considered an essential component for long-term culture of avian embryonic stem cell, primordial germ cell and embryonic germ cell and its combination with bFGF and SCF has been expected to elicit much higher effect (Pain et al., 1996; Park et al., 2000). The effect of each growth factor except for SCF was worse than the control (DMEM-C) (see FIG. 5); however, the media containing different combinations of LIF, bFGF, IGF-1 and SCF exhibited significantly better effect than the control (addition of SCF: 2.8-fold, no addition of SCF: 2.2-fold), as found in this experiment. The addition of SCF to a set of other growth factors led to worse culture pattern of chicken spermatogonial stem cells than no addition of SCF, demonstrating that SCF induces differentiation and apoptosis of chicken spermatogonial stem cells (see Table 5 and FIG. 6).

TABLE 5

Culture of chicken spermatogonial stem cells using combinations of growth factors

| No. of experiment times | No. of spermatogonial stem cells (×10$^4$) | | |
|---|---|---|---|
| | DMEM-C | LIF + bFGF + IGF-1 | LIF + bFGF + IGF-1 + SCF |
| 1 | 5.8 | 14.9 | 13.9 |
| 2 | 6.9 | 15.6 | 13.0 |
| 3 | 6.1 | 16 | 14.2 |
| 4 | 5.7 | 17.9 | 13.6 |
| 5 | 5.3 | 16 | 11.9 |
| Mean ± SD | 5.96 ± 0.535 | 16.08 ± 0.994 | 13.32 ± 0.813 |

6) Influence of Culture Temperature on Culture of Spermatogonial Stem Cell

Figure 7:
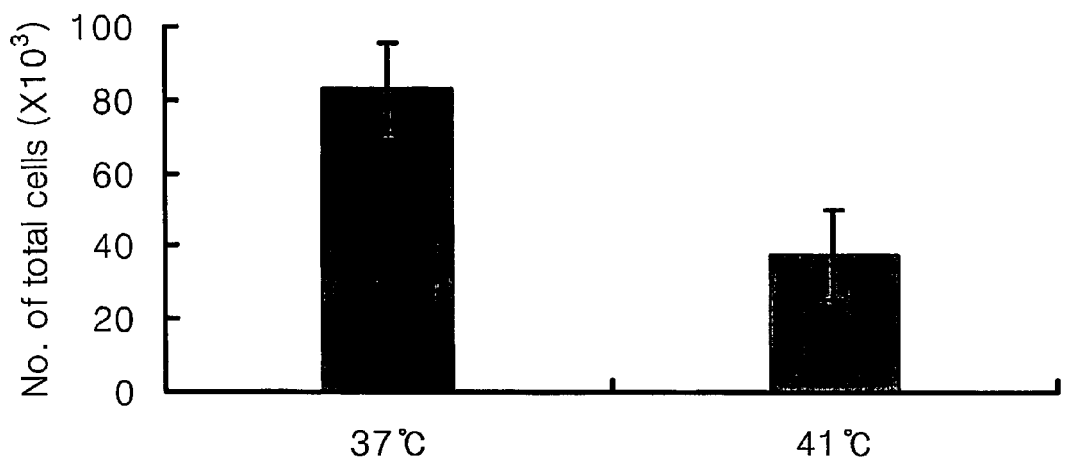
FIG. 7 is a graph showing the number of chicken spermatogonial stem cells depending on culturing temperatures.

Aves such chicken have body temperature (41° C.) higher than mammals and their testis exist inside body. Therefore, the culture of testicular cells was carried out at 37° C. (conventional culture temperature) and 41° C. (body temperature of chicken) and the number of spermatogonial stem cells was compared. It was observed that the number of spermatogonial stem cells cultured at 37° C. was about 2.2-fold larger than those cultured at 41° C. (see Table 6 and FIG. 7). Interestingly, it has been reported that the number of mouse spermatogonial stem cells cultured shows no significant difference between at 37° C. and at 32° C. (optimal temperature of in vitro culture of testicular cells) (Nogano et al., 2003).

TABLE 6

Number of chicken spermatogonial stem cells depending on culture temperature

| No. of experiment times | No. of spermatogonial stem cells (×10³) | |
|---|---|---|
| | 37° C. | 41° C. |
| 1 | 73 | 27 |
| 2 | 98 | 51 |
| 3 | 78 | 35 |
| Mean ± SD | 83.0 ± 13.2 | 37.6 ± 12.2 |

7) Growth Curve of Chicken Spermatogonial Stem Cells

Testicular cells of mammals such as mouse may be isolated in a considerably small number and their larger portion dies in in vitro culture, making it difficult to culture testicular cells. Testicular cells of aves such as chicken show similar culture pattern to those of mammals; however, their isolation provides much larger cells than mammals. Chicken spermatogonial stem cells were cocultured with gonadal stroma cells because their culture is dependent on feeder cells. Since the number of chicken spermatogonial stem cells (about 0.08%) was relatively larger than that of mouse spermatogonial stem cells, it could be measured after culturing even though their large portion dies during in vitro culture.

Figure 8:
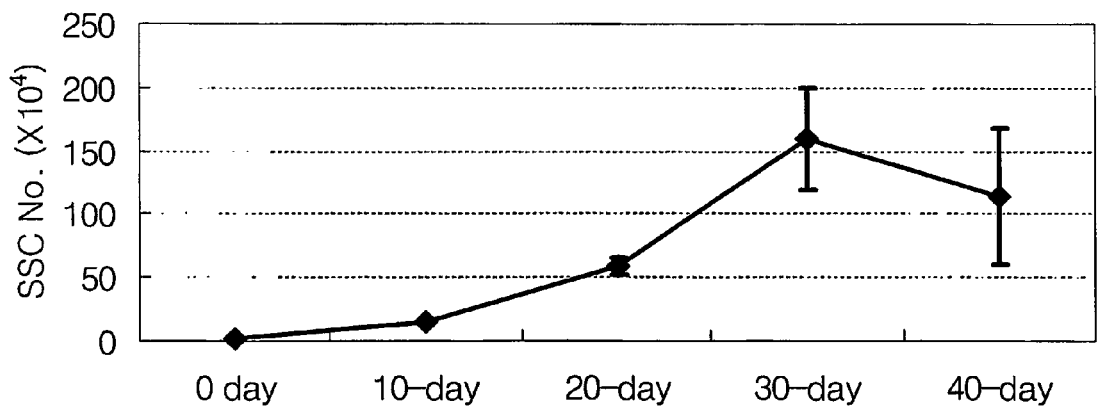
FIG. 8 is a growth curve of in vitro cultured chicken spermatogonial stem cells.

Subculturing was performed at an interval of about 10 days. The number of spermatogonial stem cells was gradually increased until 3 passages and in turn their large potion died (see FIG. 8). Following apoptotic cell death of a large number of spermatogonial stem cells after passage 4, the total cell number was decreased and only spermatogonial stem cells continued to divide.

8) Establishment of Long-Term Culture Conditions of Avian Spermatogonial Stem Cells Researches for the culture (particularly, long-term culture) of spermatogonial stem cells derived from aves such as chicken have not been yet reported. Instead, it has been reported that spermatogonial stem cells of mice (Nagano et al., 2001; Kanatsu-Shinohara et al., 2003) and calf (Izadyar et al., 2003) were cultured for about 5 months. Most of spermatogonial stem cells are very likely to die at initial stage of culture, which makes it difficult to culture them.

Figure 9:
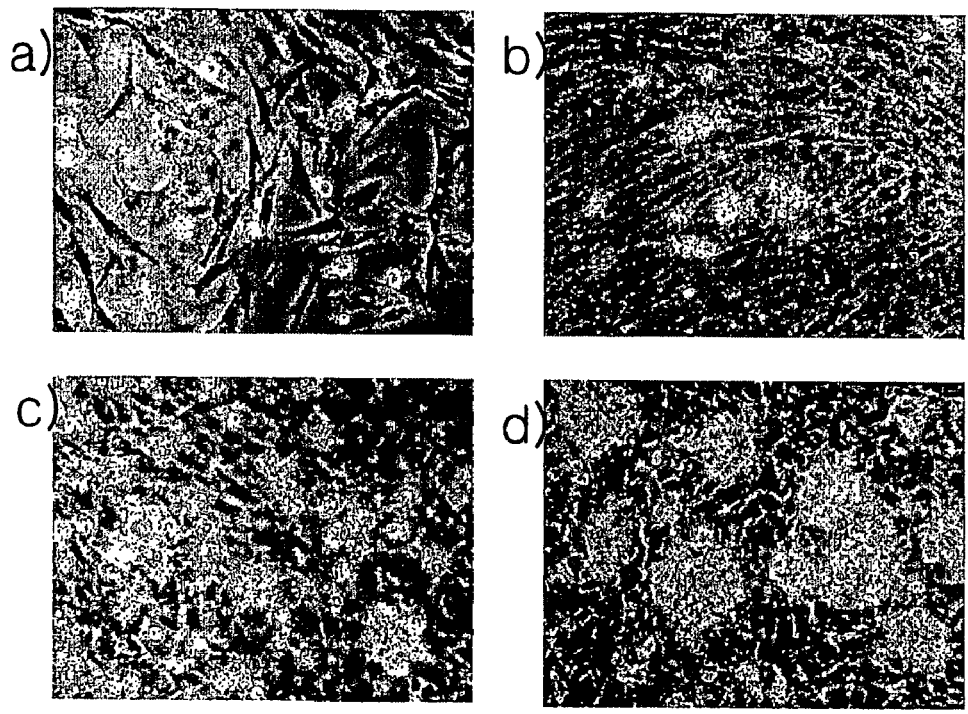
FIG. 9 is photographs demonstrating the culture patterns of chicken spermatogonial stem cells (200×). (a) primary culture for 3 days, (b) primary culture for 7 days, (c) subculture (passage 1) for 5 days, (d) subculture for about 3 months (cultured for 20 days after passage 6).

For culturing chicken spermatogonial stem cells, the total of testicular cells were cultured for about 10 days as a primary culture (see FIGS. 9(a) and (b)) and spermatogonial stem cells forming colonies were taken, after which they were cultured on feeder layers in culture dishes (see FIGS. 9(c) and (d)). At initial stage of culture, Sertoli cells grew more rapidly and small-sized colonies formed by 3-4 cells were observed (see FIG. 9(b)). Where spermatogonial stem cells collected were cocultured with gonadal stroma cells (GSC), their number were sharply increased (see FIG. 9(c)). Furthermore, spermatogonial stem cells proliferated to form colonies after subculturing, demonstrating that long-term in vitro culture of chicken spermatogonial stem cells could be successfully carried out for more than 3 months (see FIG. 9(d)). Therefore, it would be appreciated that the present invention allows chicken spermatogonial stem cells to be cultured for about 5 months even though a little variation of culturing period may occur depending on the week age of chicken. For example, spermatoginal stem cells derived from 2-4 week-old chicken was long-term cultured with more difficulty than those of 5-8 week-old chicken due presumably to the differentiation to type B spermatogonial cell after 5-week age.

9) Characterization of Spermatogonial Stem Cells by Immunocytochemical Methods

Since morphological and molecular markers to discriminate spermatogonial stem cells of animals such as chicken, mouse and rat have not yet been suggested in a reliable manner, various attempts have been made. It has been reported that α6-integrin and β1-integrin are specific to gonocyte and spermatogonia of mice (Shinohara et al., 1999). The present inventors examined staining patterns for isolated testicular cells and cultured spermatogonial stem cells using antibodies to α6-integrin and β1-integrin, PAS stain and STA.

(i) PAS Staining

Chicken primordial germ cells and embryonic germ cells are stained purplish red by PAS staining due to the presence of a rich amount of glycogen in cytoplasm, which renders them to be discriminated from other types of cells (Meyer, 1964; Park et al., 2000). In particular, chicken embryonic germ cells are specifically stained by PAS staining even after long-term culture.

Figure 10:
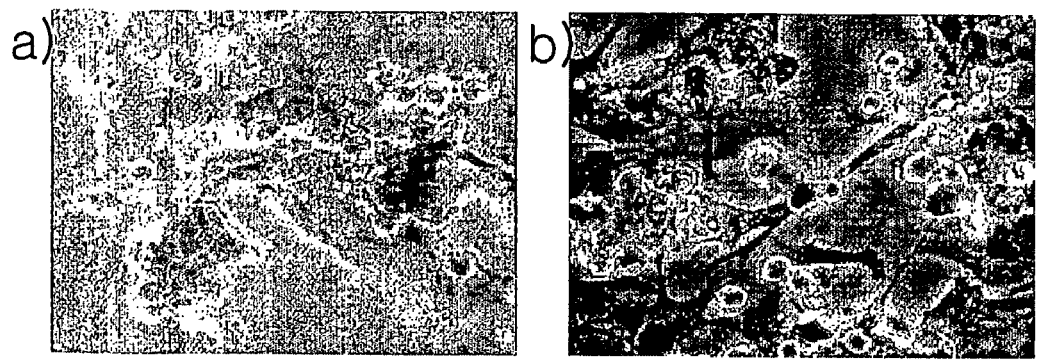
FIG. 10 is photographs representing PAS staining results of in vitro cultured chicken spermatogonial stem cells (200×). (a) spermatogonial stem cells of 4-week-old chicken (passage 2), (b) spermatogonial stem cells of 9-week-old chicken (passage 2).

Chicken spermatogonial stem cells were stained using a PAS kit in consideration of the fact that they are originated from primordial germ cells. Like PGC and EG cell, they were stained purplish red. PAS staining showed its specificity to spermatogonial stem cells derived from testes of both 4-week-old and 9-week-old chicken. Such staining feature makes it possible to discriminate chicken spermatogonial stem cells from Sertoli cell and other cells (see FIG. 10).

(ii) STA-FITC and DBA-FITC Staining

Figure 11A:
FIG. 11a is photographs representing FITC-STA staining results of in vitro cultured chicken spermatogonial stem cells (400×). Spermatogonial stem cells of 3-week-old chicken (passage 2) were reacted on their surface with FITC-STA to emit fluorescence. (a) a photograph taken under a fluorescence microscope, (b) a photograph taken under a phase contrast microscope.
Figure 11A:
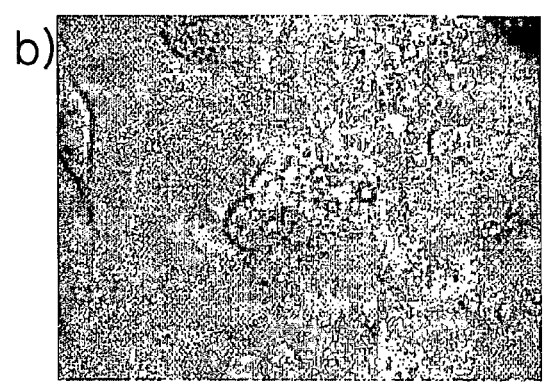
Figure 11B:
FIG. 11b is photographs representing FITC-DBA staining results of in vitro cultured chicken spermatogonial stem cells. Panels (a) and (b) correspond to chicken spermatogonial stem cells at passage 0 and panels (c) and (d) correspond to chicken spermatogonial stem cells at passage 3. Panels (a) and (c) are photographs under a fluorescence microscope, and panels (b) and (d) are photographs under a phase contrast microscope.
Figure 11B:
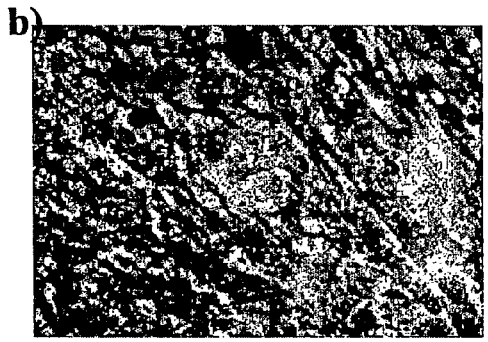
Figure 11B:
Figure 11B:
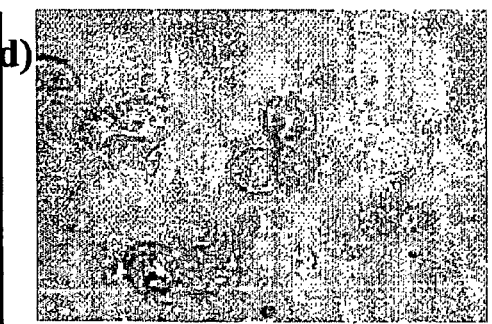

To reveal the specific staining of chicken spermatogonial stem cells to lectins, DBA (*Doliclos bifflrus* agglutinin), STA (*Solanum tubersum* agglutinin), WGA (*Triticum vulgaris* agglutinin) and ConA (*Canavalia ensiformis* agglutinin) were examined. As a result, WGA was reactive to spermatogonial stem cells as well as feeder cells and ConA to feeder cells. It was observed that STA was specifically reacted to spermatogonial stem cells not feeder cells. Such specific staining performance was also observed even after long-term culture (passage 8), suggesting that STA can play a role as a specific marker for chicken spermatogonial stem cells (see FIG. 11a). These staining results teach that (N-acetylglucosamine)3 recognized by STA specifically exists on chicken spermatogonial stem cells. In addition, DBA was reacted specifically to chicken spermatogonial stem cells. The same staining pattern with DBA was also observed even after long-term culture (passage 3), demonstrating that DBA can serve as a specific marker for chicken spermatogonial stem cells (see FIG. 11b).

In the meantime, Izadyar et al. (2002) have verified that DBA specifically reactive to bovine spermatogonial stem cells could be used in purification of spermatogonial stem cells and serve as interspecies differentiation marker after xenotransplantation. In this connection, the present experimental results show that STA and DBA could be used in purification of chicken spermatogonial stem cells and serve as interspecies differentiation marker after xenotransplantation.

(iii) Reactivity of Chicken Spermatogonial Stem Cells to α6-Integrin and β1-Integrin Both α6-integrin and β1-integrin form a heterodimer in cells and play an essential role in signal transduction. Specifically, α6-integrin and β1-integrin serve as a specific marker for mouse spermatogonial stem cells (Shinohara et al., 1999).

Figure 12:
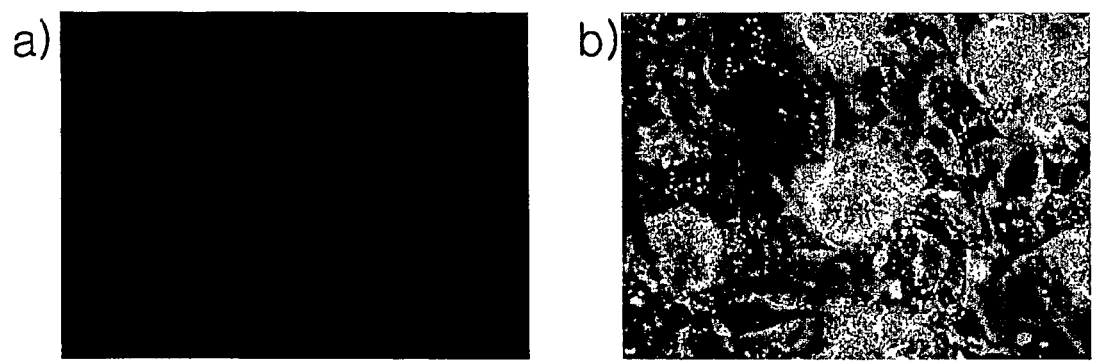
FIG. 12 is photographs representing α6-integrin antibody staining results of in vitro cultured chicken spermatogonial stem cells (200×). Spermatogonial stem cells (passage 1) derived from 3-week-old chicken were used.
Figure 13:
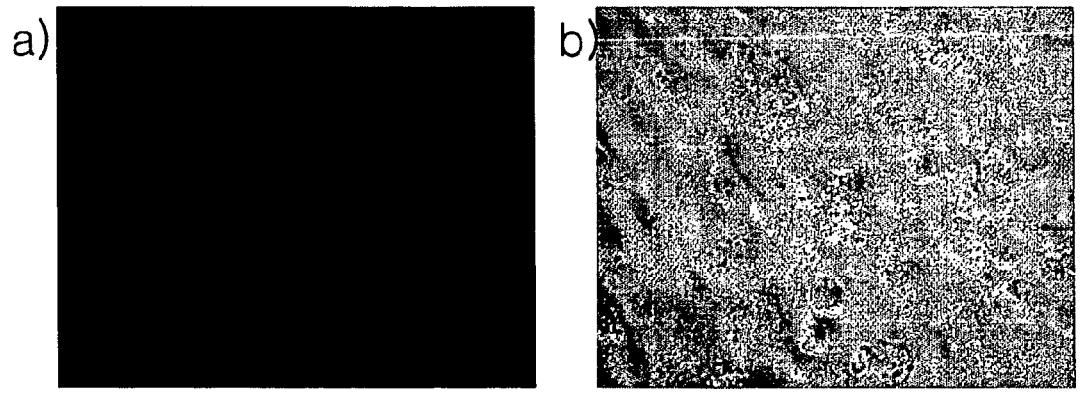
FIG. 13 is photographs representing anti-β1-intergrin antibody staining, results of in vitro cultured chicken spermatogonial stem cells (200×). Spermatogonial stem cells (passage 1) derived from 3-week-old chicken were used.

It was also shown that chicken spermatogonial stem cells were specifically reactive to α6-integrin and β1-integrin (see FIGS. 12 and 13). It was observed that α6-integrin was reactive to the surface of chicken spermatogonial stem cells with higher specificity than β1-integrin. It could be presumed that growth or inhibitory factors secreted by feeder cells under the control of α6-integrin and β1-integrin affect the overall signal transduction (i.e. signal transduction for differentiation or apoptosis) of chicken spermatogonial stem cells.

(iv) Anti-SSEA-1, SSEA-3 and SSEA-4 Antibody Staining

Figure 14:
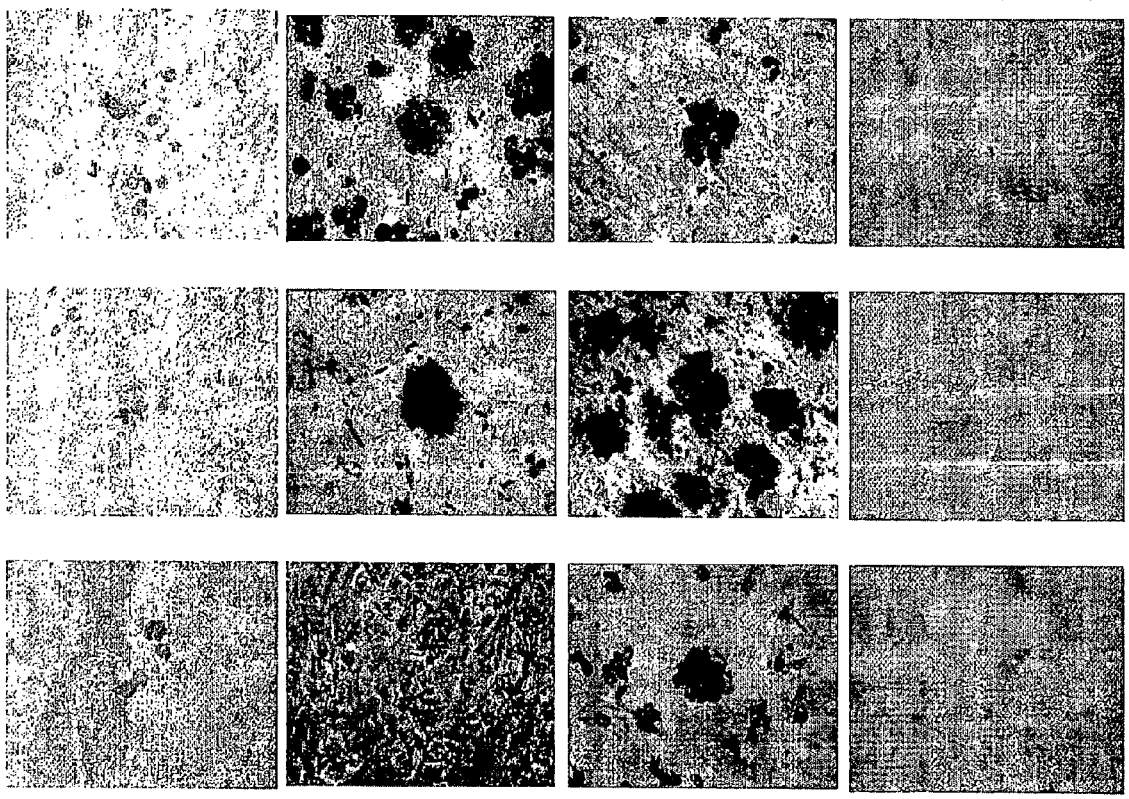
FIG. 14 is photographs representing anti-SSEA-1, SSEA-3 and SSEA-4 antibody immunostaining results of in vitro cultured chicken spermatogonial stem cells. P denotes the number of passage and TSC denotes chicken testis stroma cell.

While anti-SSEA-1, SSEA-3 and SSEA-4 antibody has been known to serve as a maker for mouse spermatogonial stem cells, there are no reports about their role as a chicken spermatogonial stem cell-specific marker. As shown in FIG. 14, it was observed that anti-SSEA-1, SSEA-3 and SSEA-4 antibody were specifically expressed on chicken spermatogonial stem cells whereas TSC (testicular stromal cell) was not completely stained with anti-SSEA-1, SSEA-3 and SSEA-4 antibody. Therefore, it could be understood that anti-SSEA-1, SSEA-3 and SSEA-4 antibody can be used as a marker specific to chicken spermatogonial stem cells.

(v) Double Immunostaining

Figure 15:
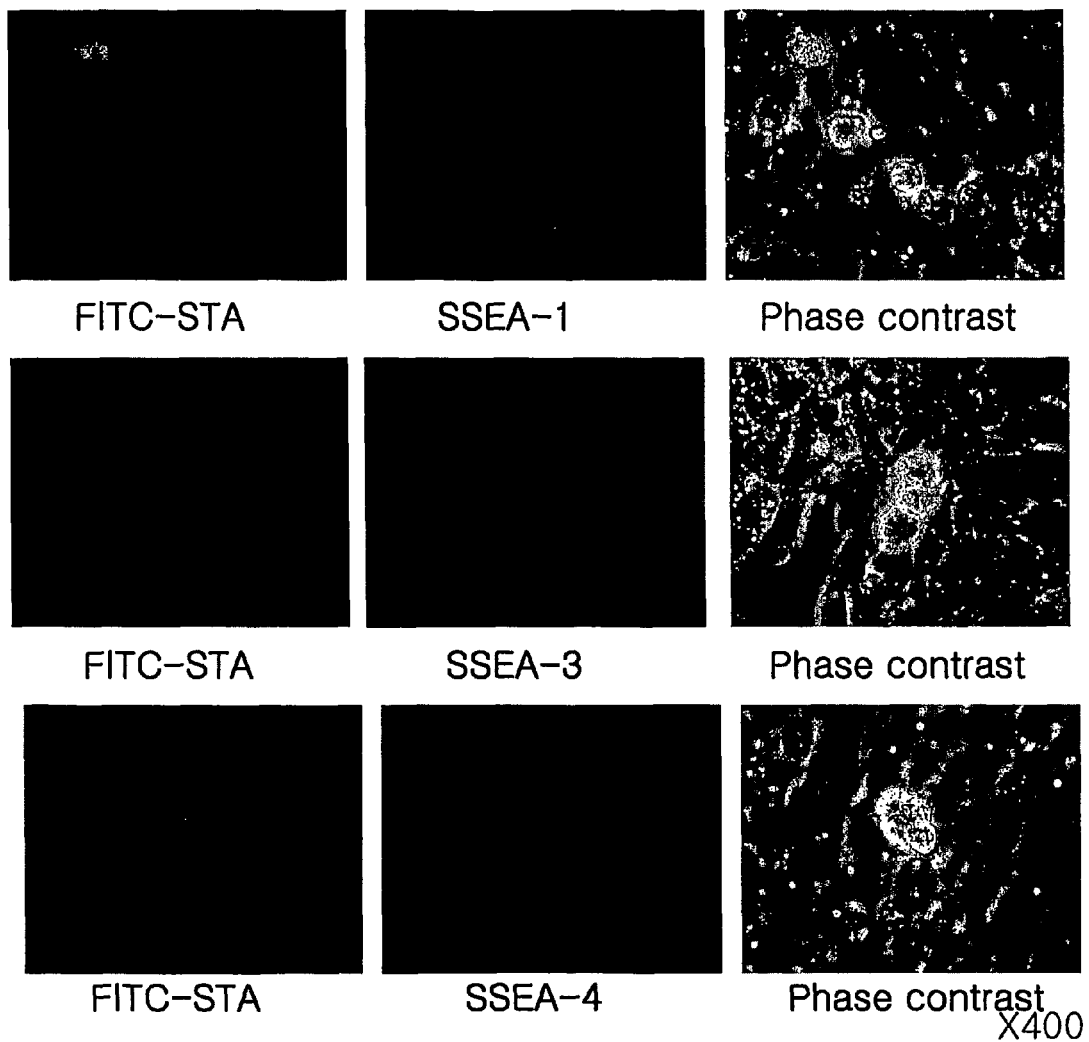
FIG. 15 is photographs representing the results of the double staining of in vitro cultured chicken spermatogonial stem cells by use of FITC-STA and anti-SSEA-1 antibody.

As represented in FIG. 15, chicken spermatogonial stem cells were positive to the double staining with anti-SSEA-1 antibody and FITC-STA.

Chicken spermatogonial stem cells identified through a series of experiments including cell culture and characterization were denoted as "chSSC" and deposited on Jun. 14, 2003 in the International Depository Authority, the Korean Cell Line Research Foundation under the accession number KCLRF-BP-00080.

As described previously, the present invention provides a method for long-term culturing of avian spermatogonial stem cells, a population of avian spermatogonial stem cells and a transgenic ave. According to the present invention, avian spermatogonial stem cells can be prepared in more reliable manner. Avian spermatogonial stem cells prepared are helpful in understanding t principle underlying spermatogenesis. In addition, avian spermatogonial stem cells of this invention are useful in producing transgenic aves with gene manipulation.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

Chen, H. Y., et al., (1990) Vectors, promoters & expression of genes in chick embryo, J. Reprod. Fert. 41:173-182.

Dirami G., et al., (1999) Effects of stem cell factor and granulocyte macrophage-colony stimulating factor on survival of porcine type A spermatogonia cultured in KSOM. Biol Reprod. 61:225-230.

Dobrinski, I. et al., (2000) Germ Cell Transplantation From Large Domestic Animals Into Mouse Testes. Mol. Reprod. Dev. 57:270-279.

Ertl, C. and Wrobel K. H. (1992) Distribution of sugar residues in the bovine testis during postnatal ontogenesis demonstrated with lectinhorseradish peroxidase conjugates Histochemistry 97:161-171.

Feng, L.-X., et al., (2002) Generation and in Vitro Differentiation of a Spermatogonial Cell Line. Science 297:392-395.

Izadyar F., et al., (2002) Isolation and purification of type A spermatogonia from the bovine testis. Reproduction 124: 85-94.

Izadyar, F., et al., (2003) Proliferation and Differentiation of Bovine Type A Spermatogonia During Long-Term Culture. Biol Reprod 68:272-281.

Kanatsu-Shinohara M., et al., (2003) Long-term proliferation in culture and germline transmission of mouse male germ-line stem cells. Biology of Reproduction. [Epub ahead of print].

Kopchick, J. J. et al., (1991) Methods for the introduction of recombinant DNA into chicken embryos. In Transgenic Animals, ed.

N. L. First & F. P. Haseltine, pp. 275-293, Boston; Butter-worth-Heinemann.

Lee, M.-R. and Shuman, R. (1990) Transgenic quail produced by retrovirus vector infection transmit and express a foreign gene marker. Proc. 4th World Congr. Genet. Appl. Livestock Prod. 16, 107-110.

Matsui Y., Zsebo K. and Hogan B. L. M. (1992) Derivation of pluripotential embryonic stem cells from murine primordial germ cells in culture. Cell 70:841-847.

Meistrich M. L., van Beek MEAB. (1993) Spermatogonial stem cells. In: Desjardins C, wing LL (eds.), Cell and Molecular Biology of the Testis. New York: Oxford University Press; 266-295.

Meng X., et al., (2000) Regulation of cell fate decision of undifferentiated spermatogonia by GDNF. Science 287: 1489-1493.

Meyer D. B. (1964) The migration of primordial germ cells in the chick embryo. Developmental Biology 10:154-190.

Morrison S. J., et al., (1997) Regulatory mechanisms in stem cell biology. Cell 88:287-298.

Nagano M, et al., (2001) Transgenic mice produced by retro-viral transduction of male germ-line stem cells. Proc Natl Acad Sci USA 98:13090-13095.

Nagano, M., et al., (1998) Culture of mouse spermatogonial stem cells. Tissue Cell 30, 389-397.

Nagano, M., et al., (2003) Maintenance of mouse male germ line stem cells in vitro. Biol Reprod. [Epub ahead of print]

Ogawa T., et al., (1997) Transplantation of testis germinal cells into mouse seminiferous tubules. Int J Dev Biol 41:111-122.

Ogawa, T. (2001) Spermatogonial transplantation: the principle and possible application. J. Mol. Med. 79:368-374.

Pain B., et al., (1996) Long-term in vitro culture and characterization of avian embryonic stem cells with multiple morphogenetic potentialities. Development 122:2339-2348.

Park T. S. and Han J. Y. (2000) Derivation and Characterization of Pluripotent Embryonic Germ Cells in Chicken. Molecular Reproduction and Development 56:475-482.

Rassoulzadegan M., et al., (1993) Transmeiotic differentiation of male germ cells in culture. Cell 75:997-1006.

Resnick J. L., et al., (1992) Long-term proliferation of mouse primordial germ cells in culture. Nature 359: 550-551.

Russell L. D., et al., (1990) Histological and Histopathological Evaluation of the Testis. Clearwater, Ill.: Cache River Press. pp 158.

Shinohara, T., et al., (1999) 1- and 6-integrin are surface markers on mouse spermatogonial stem cells. Proc. Natl. Acad. Sci. 96:5504-5509.

Sousa, M., et al., (2002) Developmental potential of human spermatogonial cells co-cultured with Sertoli cells. Human Reprod. 17(1):161-172.

Tegelenbosch R. A. and de Rooij D. G. (1993) A quantitative study of spermatogonial multiplication and stem cell renewal in the C3H/101 F1 hybrid mouse Mutation Research 290 193-200.

VAN Pelt A. M., et al., (2002) Establishment of Cell Lines with Rat Spermatogonial Stem Cell Characteristics. Endocrinology 143:1845-1850.

van der Wee K. S., et al., (2001) Immunomagnetic isolation and long-term culture of mouse type A spermatogonia. J Androl. 22: 696-704.

van Pelt A. M., et al., (1996). Isolation of the synchronized A spermatogonia from adult vitamin A-deficient rat testes. Biol Reprod 55(2):439-444.

Wong, T. K. et al., (1980) *Gene,* 10:87.

Yan W. Suominen J. and Toppari J. (2000) Stem cell factor protects germ cells from apoptosis in vitro. J. Cell Science 113: 161-168.

What is claimed is:

1. A method for a long-term culture for more than 3 months of avian spermatogonial stem cells, which comprises the steps of:
(a) preparing an avian testis from an avian aged 2-70 weeks;
(b) isolating a population of testicular cells from said avian testis;
(c) culturing said population of testicular cells for about 5 to 10 days on plates in a medium containing a cell growth factor to form a colony of spermatogonial stem cells; and
(d) taking a colony of spermatogonial stem cells and culturing said avian spermatogonial stem cells for more than about 80 to 85 days on a feeder cell layer in a medium containing a cell growth factor;
wherein said step (b) is carried out by treating said avian testis with a mixture of collagenase and trypsin; said medium in steps (c) and (d) includes FBS (fetal bovine serum), avian serum, non-essential amino acids, Hepes buffer, and β-mercaptoethanol; and said feeder cell is avian gonadal stroma cell or testicular stroma cell.

2. The method according to claim 1, wherein said cell growth factor is a growth factor selected from the group consisting of fibroblast growth factor, insulin-like growth factor-1, stem cell factor, glial-derived neurotrophic factor and their combination.

3. The method according to claim 1, wherein said medium further comprises a differentiation inhibitory factor.

4. The method according to claim 3, wherein said differentiation inhibitory factor is leukemia inhibitory factor.

5. The method according to claim 1, wherein said medium comprises a supplement containing a mixture of fibroblast growth factor, insulin-like growth factor-i and leukemia inhibitory factor.

6. The method according to claim 1, wherein said medium further comprises a serum and an antioxidant.

7. The method according to claim 1, wherein said culturing is carried out at about 37° C.

8. The method according to claim 1, wherein said avian species is a chicken, a quail, a turkey, a duck, a goose, a pheasant or a pigeon.

9. The method according to claim 1, wherein after step (c) said process further comprises the step of identifying the avian spermatogonial stem cells.

10. The method according to claim 9, wherein said identification is carried out by (i) PAS (Periodic Acid Shift's) staining, (ii) STA (*Solanum tubersum* agglutinin) staining, (iii) a staining with α6-integrin antibody, (iv) a staining with β1-integrin antibody, (v) a staining with anti-S SEA-1 antibody, (vi) a staining with anti-SSEA-3 antibody, (vii) a staining with anti-S SEA-4 antibody, (viii) DBA (*Doliclos biffirus* agglutinin) staining or (ix) their combination.

11. The method of claim 1, wherein said avian is aged up to 20 weeks.

12. The method of claim 11, wherein said avian is aged 2-10 weeks.

13. The method of claim 1, wherein said avian is a chicken.

14. The method of claim 12, wherein said avian is a chicken.

15. A method for a long-term culture for more than 3 months of avian spermatogonial stem cells, which comprises the steps of:
(a) preparing an avian testis from an avian that is not in an embryonic stage;
(b) isolating a population of testicular cells from said avian testis; and
(c) culturing said population of testicular cells for about 5 to 10 days on plates in a medium containing a cell growth factor to form a colony of spermatogonial stem cells; and
(d) taking a colony of spermatogonial stem cells and culturing said avian spermatogonial stem cells for more than about 80 to 85 days on a feeder cell layer in a medium containing a cell growth factor;
wherein said step (b) is carried out by treating said avian testis with a mixture of collagenase and trypsin; said medium in steps (c) and (d) includes FBS (fetal bovine serum), avian serum, non-essential amino acids, Hepes buffer, and β-mercaptoethanol; and said feeder cell is avian gonadal stroma cell or testicular stroma cell.

* * * * *